United States Patent [19]

Liang

[11] 4,404,144

[45] Sep. 13, 1983

[54] UNSATURATED ANALOGS OF β-ALKYL-β-HYDROXY GLUTARIC ACID AND ESTERS THEREOF

[75] Inventor: Chi-Dean Liang, Glenview, Ill.

[73] Assignee: G. D. Searle & Co., Skokie, Ill.

[21] Appl. No.: 327,821

[22] Filed: Dec. 7, 1981

Related U.S. Application Data

[63] Continuation-in-part of Ser. No. 236,092, Feb. 20, 1981, abandoned.

[51] Int. Cl.$^3$ ............... C07C 69/675; C07C 69/732; C07C 59/185; C07C 59/245; C07C 59/58; C07C 59/76; C07C 49/175; C07C 49/255

[52] U.S. Cl. .......................... 260/410.9 R; 562/582; 568/415; 260/413; 560/181

[58] Field of Search ............... 560/181, 183; 562/582; 260/413 K, 413 R, 413 M, 413 Q, 410.9 M, 410.9 Q; 568/415

[56] References Cited

U.S. PATENT DOCUMENTS 3,818,080  6/1974  Baran et al. ..................... 562/582

Primary Examiner—Natalie Trousof
Assistant Examiner—L. Hendriksen
Attorney, Agent, or Firm—James G. Passe

[57] ABSTRACT

This invention relates to β-Alkyl-β-Hydroxy Glutaric acid ∂ ester derivatives which are useful as anti-hyperlipoproteinemia agents.

15 Claims, No Drawings

UNSATURATED ANALOGS OF β-ALKYL-β-HYDROXY GLUTARIC ACID AND ESTERS THEREOF

BACKGROUND OF THE INVENTION

The present application is a continuation-in-part of patent application Ser. No. 06/236,092 filed Feb. 20, 1981, now abandoned.

The present invention provides novel compounds. In particular, this invention relates to analogs of β-alkyl-β-Hydroxy-Glutaric acid and esters.

The compounds of the present invention are useful as anti-hyperbetalipoproteinemia agents which are used to treat a mammal suffering from or susceptible to the development of an atherosclerotic disease.

Atherosclerosis in mammals is a disease characterized by the deposition of atherosclerotic plaque on arterial walls. While atherosclerosis exhibits many varies forms and consequences, typical consequences of atherosclerotic diseases include angina pectoris, myocardial infarction, stroke and transient cerebral ischemic attacks. Other forms of atherosclerotic diseases include certain peripheral vascular diseases and other ischemias (e.g., bowel and renal).

Medical science now recognizes that certain forms of atherosclerosis may be preventable or reversible. Agents capable of preventing or reversing atherosclerosis are characterized as exhibiting antiatherosclerotic activity. Since serum lipids have a recognized association with atherogenesis, an important class of antiatherosclerotic agents are those with serum lipid-modifying effects. Serum lipids implicated in atherogenesis include serum cholesterol, serum trighycerides, and serum lipoproteins.

With respect to serum lipoproteins, at least three different classes of these substances have been characterized; high density lipoproteins (HDL's), low density lipoproteins (LDL's and VLDL's levels (anti-hyperbetalipoproteinemic activity) is postulated to have a direct antiathrtosclerotic effect. See Goodman and Gilman, The Pharmacological Basis of Terapeutics, fourth Ed. 764–766 (1971). The importance of lowering cholesterol levels may further be demonstrated by the availability of several commercial prescription products that are designed to lower cholesterol by several routes. See Physicians Desk Reference 1977, Choloxin pg. 823, Atromid S pg. 583, Cytellin pg. 947, and Questran pg. 1048. Several mechanisms of action have been described, for example, stimulation of the liver to increase catabolism and excresion of cholesterol, blocking the absorption of cholesterol in the intestine, and elimination by emulsification. The compounds of the present invention inhibit the production of cholesterol directly. This is beneficial in that serum liprotein levels of cholesterol are kept low without the need to eliminate any excess. It is therefore also beneficial in cases of hypercholesterol production.

SUMMARY OF THE INVENTION

The present invention relates to derivatives of glutaric acid and esters thereof and specifically relates to β-alkyl-β-hydroxy glutaric acid and esters represented by formula I of Chart A, where $R_1$ is $C_9$ to $C_{19}$ alkenyl or alkadienyl; $R_2$ is dialkoxymethyl or carboxy and $R_3$ is (hydroxy or alkoxy) carbonylmethyl when $R_4$ is hydroxy, or $R_3$ and $R_4$ are taken together form carbonyl oxygen; and the pharmaceutically acceptable salts thereof.

The test procedure used to determine anti-betahyperlipoproteinemia is as follows: Hepatic β-hydroxy-β-methylglutaryl coenzyme A Reductase(HMG CoA reductase) inhibition is measured in the rat. Rats used are males weighing from 180–220 g pretreated with 2% Diethylaminoethanolamine in diet using reversed lighting. 1 millimolar final concentration of test compound is used in liver in Vitro testing. Activity for each compound is reported as a percent inhibition based on control. A compound is considered active if it inhibits the conversion of $^{14}C$-Hydroxymethylglutaryl-CoA to $^{14}C$-mevalonolactone in the prescribed assay by 40% or more. If significant activity is observed, a titration will be done to determine potency and affinity for enzyme relative to substrate. HMG CoA reductase is the rate controlling enzyme in the synthesis of cholesterol. An agent which inhibits the enzymatic activity would be expected to reduce conversion or precursors to cholesterol. Therefore, an agent which inhibits this enzyme should be beneficial in the treatment of hyperlipoproteinemia with enhanced cholesterol biosynthesis.

The term lower alkyl, as used herein, refers to straight or branched chain alkyl groups having from 1 to 6 carbon atoms, i.e., methyl, ethyl, n-propyl, iso-propyl, n-butyl, sec-butyl, tert-butyl, n-pentyl, 2,2-dimethylpropyl, n-hexyl, 2-methylpentyl, 2,2-dimethylbutyl, etc.

The term "pharmaceutically acceptable salts" refers to cationic salts such as the sodium, potassium, calcium, magnesium, aluminum, ammonium, etc. salts.

The mammals susceptible to the development of atherosclerotic diseases and the untoward consequences thereof are particularly those physically asymptomatic patients manifesting one or more risk factors known to predispose one to disease development. Such risk factors are high serum cholesterol and serum triglycerides, hypertension, obesity, diabetes, and genetic predisposition. Mammals manifesting two or more risk factors are deemed to be especially susceptible to atherosclerotic diseases. Accordingly, in using the compound of the invention for the instant purposes, an oral route of administration, either by conventional oral dosage forms or by mixture with food or feed, represents the preferred method of their systemic administration. Alternatively, however, these compounds may be administered by other convenient routes of administration whereby systemic activity is obtained. These other routes of administration would, accordingly, include rectal, vaginal, subcutaneous, intravenous, and the like routes.

Liquid dosage forms for oral administration include pharmaceutically acceptable emulsions, solutions, suspension, syrups, and elixirs containing inert diluents commonly used in the art, such as water. Besides, such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

The compounds of the present invention are useful antihyperbetalipoproteinemic agents at dosages from 5 to 250 mg/kg daily preferably in divided dosages. The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment.

DESCRIPTION OF THE PREFERRED EMBODIMENTS

The operation of this invention is further elaborated by the representative example below.

EXAMPLE 1

Preparation of linoleyl iodide

A solution of linoleyl alcohol (5.32 g, 200 mmole) and pyridine (40 ml) was cooled to 0° C. and added to p-toluene-sulfonic chloride (4.2 g, 220 mmole) in 10 ml of pyridine. The resulting solution was stirred overnight at 0° C. and poured into 50 ml of ice water. The organic layer was extracted with 100 ml of ether and the organic layer was washed with 1% aqueous hydrochloric acid until acidic and then washed three times with water. The organic solution was dried over magnesium sulfate, filtered and the solvent evaporated to give 6 g of oily material having an $R_f$ of 0.3 on thin layer chromatography (20Δ ethyl acetate/Skelly B linoleyl alcohol $R_f=0.1$). To the crude tosylate (6 g, 140 mmole) was added acetone (150 ml) and sodium iodide (300 mmole, 4.5 g), and the mixture was heated gently on a steam bath for 3 hours. The solvent was removed in vacuo and 200 ml of ether added thereto. The organic layer was washed twice with an aqueous solution of sodium bisulfite, twice with water and dried over magnesium sulfate, and solvent removed. The crude iodide was purified by column chromatography over silica gel and eluted with Skelly B to yield 5.2 g of linoleyl iodide $R_f$ ethyl acetate—Skelly B (10:90 v/v)=0.7 of formula II of Chart A.

EXAMPLE 2

Preparation of 9-decenyl iodide

9-Decenyl iodide was prepared by the method of Example 1 from 9-decene-1-ol.

EXAMPLE 3

Preparation of elaidyl iodide

Elaidyl iodide was prepared by the method of Example 1 from elaidyl alcohol.

EXAMPLE 4

Preparation of oleyl iodide

Oleyl iodide was prepared by the method of Example 1 from oleyl alcohol.

EXAMPLE 5

Preparation of 2-(2,2-diethoxyethyl)-2-(9,12-octadecadienyl)-1,3-dithiane 2-(2,2-Diethoxyethyl-1)-1,3 dithiane (4 mmole, 450 mg) in 25 ml of anhydrous tetrahydrofuran was cooled to −78° C. and n-butyl lithium (3 ml, 1.6 mmole/ml, 4.8 mmole) was added dropwise. Following the addition, the dry ice bath was removed and the solution was stirred at 0° C. for 3 hours. The solution was again colled to −78° C. and linoleyl iodide (4 mmole, 1.6 g) in 10 ml of tetrahydrofuran was added dropwise over a 5 minute period. After 30 minutes, the solution was stirred for 2 hours at −20° C. and 5 ml of aqueous 5% hydrochloric acid was added to the solution. The solution was then warmed to room temperature. Excess tetrahydrofuran was removed in vacuo and the organic material was extracted with ether, washed with water and dried to yield 2.5 g of product of formula III of Chart A. The structure was confirmed by NMR.

EXAMPLE 6

Preparation of 1,1-diethoxy-12,15-heneicosadiene-3-one

2-Linoleyl-2-(2,2-diethoxylethyl-1)-1,3 dithiane (2 g, 4 mmole) in acetone (40 ml), and water (4 ml) was heated to 50° C. Cadmium carbonate (4g) and mercuric chloride (4 g) were added and the reaction mixture was further heated at 50° C. for 15 minutes. Cadmium carbonate (2 g) was added and after 30 minutes at 50° C. potassium iodide (4.8 g) was added and the mixture was stirred at room temperature for 30 minutes. Solvent was removed in vacuo and ether was added (40 ml) thereto. The organic layer was washed thrice with saturated aqueous potassium iodide solution and was dried over maganese sulfate.

After purification through column chromatography, the desired product was obtained as heavy oil, (1.5 g) of formula IV of Chart A.

EXAMPLE 7

Preparation of ethyl 3-(2,2-diethoxyethyl)-3-hydroxy-12,15-heneicosadienoate

Isopropyl cyclohexylamine (565 mg, 4 mmole) in 10 ml of anhydrous tetrahydrofuran was cooled to −78° C. in a 3 neck round bottom flask and n-butyl lithium (2 ml, 4 mmole) was added dropwise. After 10 minutes, ethyl acetate (300 mg, 4 mmole) in 5 ml of tetrahydrofuran was added dropwise over a 15 minute period and the reaction mixture was stirred for 30 minutes at −78° C. following the addition. 1,1-Diethoxy-12,15-heneicosadiene-3-one (1.5 g) in 5 ml of tetrahydrofuran was added within 1 minute and the mixture was maintained at −78° C. for another 30 minutes. 5% Aqueous hydrochloric acid (5 ml) was added and the mixture was warmed to room temperature. Solvent was removed in vacuo and 40 ml of pentane was added. The organic layer was washed until neutral and was dried, worked up to provide 1.0 g of crude reaction mixture. After purification from column chromatography, the desired product was obtained as heavy oil (1.4 g) of formula XI of Chart B.

EXAMPLE 8

Preparation of 3-hydroxy-3-(9,12-octadecadienyl) pentanedioic acid monoethyl ether Ethyl 3-(2,2-diethoxyethyl)-3-hydroxy-12,15-heneicos-adienoate(1.4 g) was stirred with 16.5 ml of a solution consisting of 10 ml of acetic acid, 5 ml of water and 1.5 ml of tetrahydrofuran overnight at room temperature. The solution was carefully neutralized with sodium hydrogen carbonate and was made alkaline with aqueous sodium bicarbonate solution. The organic layer was extracted with 30 ml of ether and the etheral solution was washed with water thrice, worked up to provide the intermediate aldehyde as an oily material (1.2 g) NMR—CHO 9.8 $H_z$ (1H, multiplet). The aldehyde was then oxidized with Jones' reagent as follows. Crude aldehyde (1.4 g, 4 mmole) was dissolved with 50 ml of acetone and 4 ml of Jones' reagent was added dropwise over a 10 minute period. To the resulting green solution was then added 1 ml of saturated aqueous sodium bisulfite solution and the solvent was removed in vacuo.

Ether (50 ml) was added and the organic layer was washed until neutral and then dried. After the solvent was removed, the resulting acid-ester was purified through column chromatography to yield 1.1 g of product of Formula XII of Chart B. The structure was confirmed by NMR.

EXAMPLE 9

Preparation of 3-hydroxy-3-(9,12-octadecadienyl)pentanedioic acid

To 1.1 g of the compound of Example 8 in 20 ml of anhydrous toluene was added 0.5 g of 18 Crown-6 in 10 ml of toluene and to this, 1.2 g of potassium superoxide was added portion wise and the resulting solution was stirred vigorously under nitrogen overnight at room temperature. 5 ml of water was added cautiously and was followed by 40 ml of ether. 10 ml of 5Δ aqueous HCL solution was added to acidify the solution and the organic layer was dried. Work up the resulting oil was purified by column chromatography to yield 0.6 g of Formula XIII of Chart B.

EXAMPLE 10-14

In the same manner, the following compounds were prepared:
3-(9-decenyl)-3-hydroxypentanedioic acid of formula XIV of Chart B.
3-(9-decenyl)-3-hydroxypentanedioic acid of formula XXI of Chart C.
3-hydroxy-3-(9-cis-octadecenyl)pentanedioic acid monoethyl ester of formula XXII of Chart C.
3-hydroxy-3-(9-cis-octadecenyl)pentanedioic acid of formula XXIII of Chart C.
3-hydroxy-3-(trans-9-octadecenyl)pentanedioic acid monoethyl ester of formula XXIV of Chart C.
3-hydroxy-3-(9,12-octadecadienyl)pentanedioic acid of formula XXV of Chart C.

EXAMPLE 15

Tablets weighing 200 mg and having the following composition are formulated:

| Ingredient | Mg |
|---|---|
| Ethyl 3-(2,2-diethoxyethyl)-3-hydroxy-12,15-heneicosadienoate | 50 |
| Starch | 120 |
| Collodial silica | 27 |
| Magnesium stearate | 3 |

EXAMPLE 16

Sterile 10 ml ampules are prepared containing 10 mg per ml of ethyl 3-(2,2-diethoxyethyl)-3-hydroxy-12,15-heneicosadienoate 0.1 percent sodium bisulfate, 0.7 percent sodium chloride and 0.5 percent chlorobutanol as a preservative.

EXAMPLE 17

Topical aqueous formulations for administration by nose drops or nasal spray are formulated containing 1 mg of 3-hydroxy-3-(9,12-octadecadienyl)pentanedioic acid monoethyl ether, 3.8 mgm glycerine, 40 mg sorbital, 0.02 mg benzalkonium chloride and purified water q.s. 1 ml.

EXAMPLE 18

Vaginal suppositories are prepared containing 30 mg of 3-hydroxy-3-(9,12-octadecadienyl)pentanedioic acid with lactose in a base made from polyethylene glycol 300, polysorbate 80, polyethylene glycol 4000, glycerin and butylated hydroxytoluene buffered with lactic acid to an acid pH. The suppositories have an inert covering which dissolves promptly in the vagina. The covering is composed of gelatin, glycerin, water, methylparaben, propylparaben and coloring.

EXAMPLE 19

Rectal suppositories are prepared by admixing 10 mg of 3-(9-decenyl)-3-hydroxypentanedioic acid and 2Δ benzocaine in a base compounded with polysorbate 80, white beeswax and polypropylene glycol monostearate.

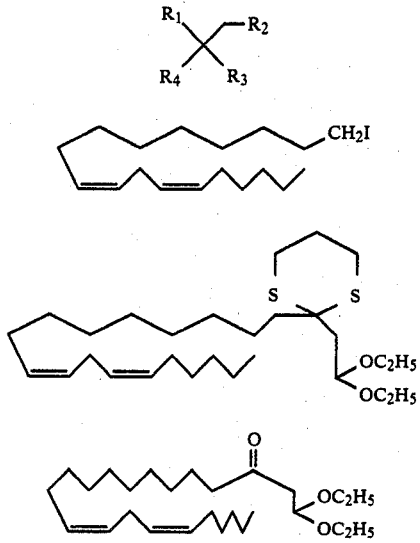

CHART A

I claim:

1. A compound of the formula $$\begin{array}{c} R_1 \diagdown \diagup R_2 \\ R_4 \diagup \diagdown R_3 \end{array}$$

wherein $R_1$ is $C_9$ to $C_{19}$ alkenyl or alkadienyl; $R_2$ is dialkoxymethyl or carboxy; $R_3$ is hydroxy or alkoxy carbonylmethyl when $R_4$ is hydroxy, or $R_3$ and $R_4$ are taken together to form a carbonyl oxygen; and pharmaceutically acceptable salts thereof.

2. A compound according to claim 1 wherein $R_2$ is —CH(OR$_5$)(OR$_6$), and $R_5$ and $R_6$ are lower alkyl; and $R_3$ and $R_4$ are taken together to form a carbonyl oxygen.

3. 1,1-Diethoxy-12,15-heneicosadien-3-one, a compound according to claim 2.

4. A compound according to claim 1 wherein $R_2$ is —CH(OR$_5$)(OR$_6$), and $R_5$ and $R_6$ are lower alkyl; $R_3$ is —CH$_2$COOR$_7$, and $R_7$ is hydrogen or lower alkyl; and $R_4$ is hydroxy.

5. A compound according to claim 4 wherein $R_7$ is hydrogen.

6. A compound according to claim 4 wherein $R_7$ is lower alkyl.

7. Ethyl 3-(2,2-diethoxyethyl)-3-hydroxy-12,15-heneicosadienoate, a compound according to claim 6.

8. A compound according to claim 1 wherein $R_2$ is —COOH; $R_3$ is —CH$_2$COOH$_7$; $R_7$ is hydrogen or lower alkyl; and $R_4$ is hydroxy.

9. A compound according to claim 8 wherein $R_7$ is hydrogen.

10. 3-Hydroxy-3-(9-decenyl)pentanedioic acid, a compound according to claim 9.

11. 3-Hydroxy-3-(cis-9-octadecenyl)pentanedioic acid monoethyl ester, a compound according to claim 8.

12. 3-Hydroxy-3-(cis-9-octadecenyl)pentanedioic acid, a compound according to claim 9.

13. 3-Hydroxy-3-trans-9-octadecenyl)pentanedioic acid monoethyl ester, a compound according to claim 8.

14. 3-Hydroxy-3-(9,12-octadecadienyl pentanedioic acid, a compound according to claim 8.

15. 3-Hydroxy-3-(9,12-octadecadienyl)pentanedioic acid monoethyl ester, a compound according to claim 8.

* * * * *